(12) United States Patent
Armstrong et al.

(10) Patent No.: US 10,294,508 B2
(45) Date of Patent: May 21, 2019

(54) METHOD AND APPARATUS FOR IDENTIFICATION OF BACTERIA

(71) Applicant: Becton, Dickinson and Company, Franklin Lakes, NJ (US)

(72) Inventors: Robert Edward Armstrong, Hunt Valley, MD (US); John Thulin Page, White Hall, MD (US); Ben Turng, Tucson, AZ (US); Glen Richard Davis, Timonium, MD (US); Strett Roger Nicolson, Owings Mills, MD (US); Timothy Hansen, Spring Grove, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 296 days.

(21) Appl. No.: 14/886,250

(22) Filed: Oct. 19, 2015

(65) Prior Publication Data
US 2016/0040210 A1 Feb. 11, 2016

Related U.S. Application Data

(62) Division of application No. 13/177,031, filed on Jul. 6, 2011, now Pat. No. 9,180,448.
(Continued)

(51) Int. Cl.
*B01L 3/00* (2006.01)
*G01N 1/00* (2006.01)
(Continued)

(52) U.S. Cl.
CPC .............. *C12Q 1/04* (2013.01); *B01L 3/0275* (2013.01); *C12Q 1/18* (2013.01); *C12Q 1/24* (2013.01);
(Continued)

(58) Field of Classification Search
CPC ......... B01L 2200/06; B01L 2200/0642; B01L 2200/0605
See application file for complete search history.

(56) References Cited

U.S. PATENT DOCUMENTS

| 3,926,733 A | 12/1975 | Chibata et al. |
|---|---|---|
| 5,094,955 A | 3/1992 | Calandra et al. |

(Continued)

FOREIGN PATENT DOCUMENTS

WO 2009065580 A1 5/2009

OTHER PUBLICATIONS

Kiestra Lab Automation, "Total Lab Automation", www.kiestra.nl/pageid=19/total_lab_automation.html, Jun. 15, 2011.
(Continued)

*Primary Examiner* — Nathan A Bowers
(74) *Attorney, Agent, or Firm* — Botos Churchill IP Law LLP

(57) ABSTRACT

An automated system for identifying in a biological sample microorganisms and their antimicrobial susceptibility (AST). The system provided an automated platform for preparing, from a single biological sample, inoculates for both ID and AST. The system loads a plate for ID testing as samples are being prepared for AST testing. The system tracks the sample and the inoculates from the samples to link the test results to the sample and the patients from whom the sample was obtained.

6 Claims, 4 Drawing Sheets

Related U.S. Application Data

(60) Provisional application No. 61/361,719, filed on Jul. 6, 2010.

(51) Int. Cl.

| | | |
|---|---|---|
| *C12Q 1/04* | (2006.01) | |
| *B01L 3/02* | (2006.01) | |
| *C12Q 1/18* | (2006.01) | |
| *C12Q 1/24* | (2006.01) | |
| *G01N 1/38* | (2006.01) | |
| *G01N 1/40* | (2006.01) | |
| *G01N 35/00* | (2006.01) | |

(52) U.S. Cl.
CPC ... *B01L 2200/0668* (2013.01); *B01L 2200/10* (2013.01); *B01L 2300/0681* (2013.01); *B01L 2400/0475* (2013.01); *G01N 1/38* (2013.01); *G01N 1/4005* (2013.01); *G01N 35/00871* (2013.01)

(56) References Cited

U.S. PATENT DOCUMENTS

| | | |
|---|---|---|
| 5,217,876 A | 6/1993 | Turner et al. |
| 5,863,754 A | 1/1999 | Bajard |
| 5,922,593 A | 7/1999 | Livingston |
| 6,096,272 A | 8/2000 | Clark et al. |
| 6,251,624 B1 | 6/2001 | Matsumura et al. |
| 6,372,485 B1 | 4/2002 | Clark et al. |
| 6,599,476 B1 * | 7/2003 | Watson .............. B65G 47/1471 141/1 |
| 6,849,422 B1 | 2/2005 | Wiles et al. |
| 7,115,384 B2 | 10/2006 | Clark et al. |
| 7,262,021 B1 | 8/2007 | Taintor |
| 8,822,167 B2 * | 9/2014 | Burd .................... B01J 19/0046 435/7.92 |
| 2002/0182114 A1 | 12/2002 | Ingenhoven et al. |
| 2002/0192676 A1 | 12/2002 | Madonna et al. |
| 2003/0124643 A1 * | 7/2003 | Taintor ................... C12Q 1/04 435/40 |
| 2006/0172370 A1 | 8/2006 | Hirleman et al. |
| 2007/0151924 A1 | 7/2007 | Mir et al. |
| 2008/0072664 A1 | 3/2008 | Hansen et al. |
| 2009/0101575 A1 | 4/2009 | Alburty et al. |
| 2010/0291669 A1 * | 11/2010 | Robinson ........... G01N 35/0099 435/287.3 |
| 2010/0330654 A1 | 12/2010 | van der Kaap et al. |

OTHER PUBLICATIONS

BD Epicenter, http://www.bd.com/ds/productCenter/BC-BactecDataManagement.asp (2009).
BD Epicenter Presentation (2006).
BD Phoenix (2008).
BD Lab.O, 20(1): 1-16 (2009).
Innovaprep, LLC Presentation (2010).
VITEK 2 Brochure (2008).
Strachan, et al., Analytica Chimica Acta, 313:63-67 (1995).

* cited by examiner

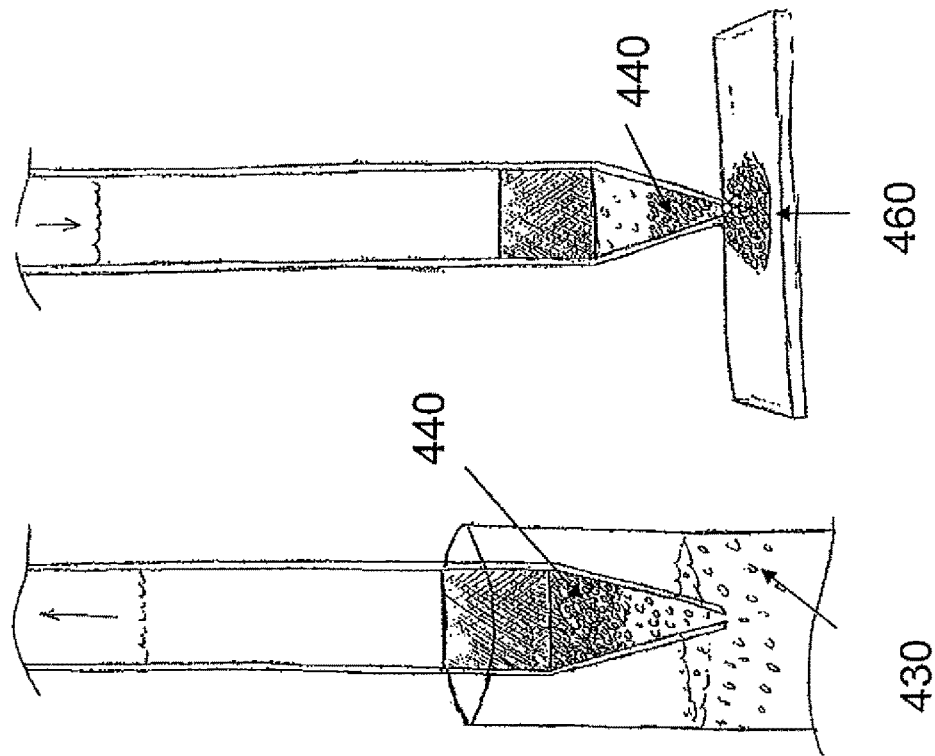
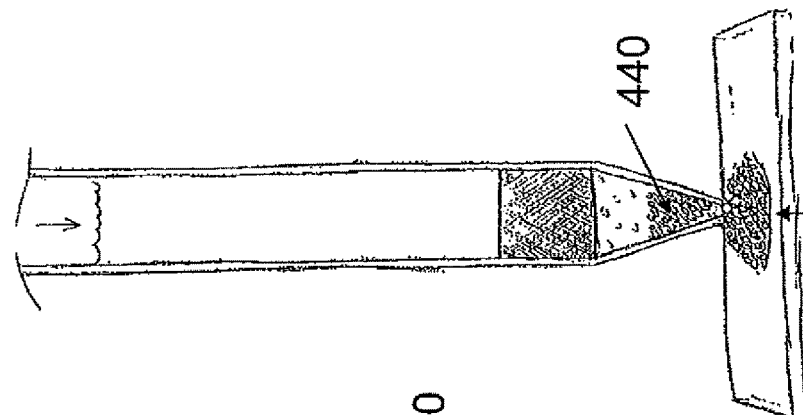
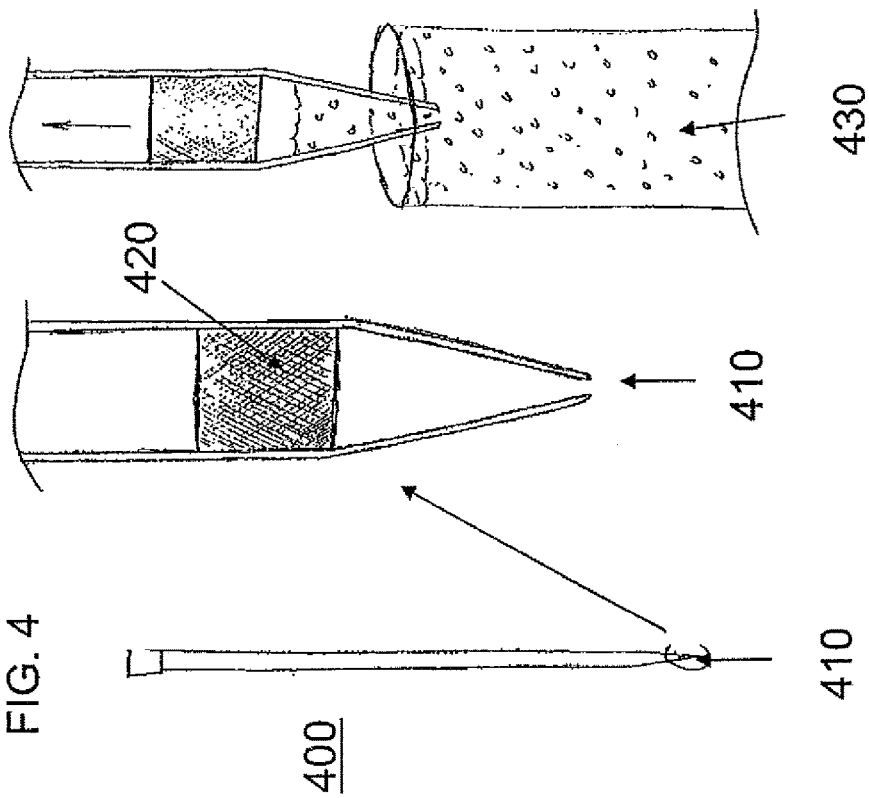
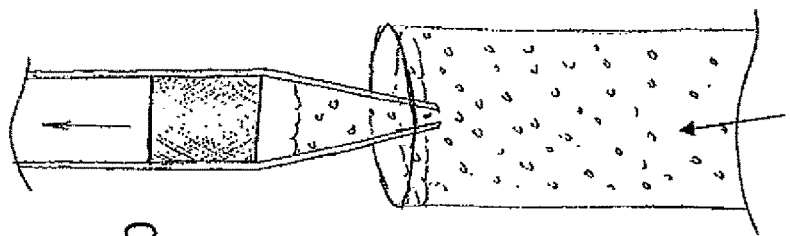

METHOD AND APPARATUS FOR IDENTIFICATION OF BACTERIA

CROSS REFERENCE TO RELATED APPLICATION

The present application is a divisional of U.S. patent application Ser. No. 13/177,031, filed on Jul. 6, 2011, which claims the benefit of the filing date of U.S. Provisional Patent Application No. 61/361,719 filed Jul. 6, 2010, the disclosures of which are hereby incorporated herein by reference.

BACKGROUND OF THE INVENTION

Disclosed herein is a system for determining both the identification and antimicrobial susceptibility of microorganisms in a biological sample (e.g. blood).

As a routine practice in medical diagnosis, biological samples such as blood are extracted from patients and analyzed. Depending upon indications, the samples may be analyzed to determine if microorganisms are present in the sample, e.g., by blood culture (such as the BACTEC™ FX and BACTEC™ 9000 series from Becton, Dickinson and Company) or by streaking onto an agar plate (manually or by an automated instrument such as the Innova™ sold by Becton, Dickinson and Company). If microorganisms are determined to be present, there is both medical and economic justification to both identify the specific microorganism present and, to facilitate treatment, the antibiotic resistance/susceptibility of the microorganism.

Many kinds of microorganism (which will also be referred to below as microbes), particularly bacteria and unicellular fungi, can be identified by mass spectrometric ("mass spec") processes, such as Matrix Assisted Laser Desorption Ionization ("Maldi"). In the Maldi process, small quantities of microbes from a colony cultivated in the usual way in a nutrient medium are transferred to a mass spectrometric sample support plate known as a Maldi plate, and then subjected directly to mass spectrometric analysis, generally by time-of-flight (TOF). The mass spectrum analysis shows the different proteins, provided they are present in the microbes in sufficient concentration. The identity of the microbe is then determined from the microbe's protein profile through a computerized search of spectral libraries containing thousands of reference spectra. If no reference mass spectrum is present in a library for the precise species of microbe being examined, computerized library searches with looser similarity requirements can provide at least some indication of the order, family or genus of the microbes, since related microbes frequently contain a number of identical protein types. The Maldi process is described in further detail in International Publication No. WO-2009/065580A1 to Ulrich Weller entitled "Identification of Pathogens in Bodily Fluids," the content of which is hereby incorporated in its entirety. A variety of mass spectrometry instruments may be used for identification.

It is desirable to analyze the effectiveness of an antimicrobial agent in inhibiting the growth of microbial isolates from clinical specimens. Such analysis is known as antimicrobial susceptibility testing ("AST"). An AST technique of the background art is a dilution technique which involves exposing bacteria to decreasing concentrations of antimicrobial agents in liquid media by serial two-fold dilution. The lowest concentration of an antimicrobial agent in which no visible bacterial growth occurs is defined as the minimal inhibitory concentration ("MIC"). The MIC is the standard measure of antimicrobial susceptibility. AST instruments are known in the art, such as the BD Phoenix™ system sold by Becton, Dickinson and Company, which performs both identification and AST.

An apparatus known in the background art that can prepare specimens for such AST processes is the BD Phoenix™ AP, available from Becton, Dickinson and Company. The workflow typically includes preparing an inoculum, such as by labeling the appropriate tube, selecting microbial colonies and making a heavy suspension in ID broth tubes, and placing the tubes in one or more racks holding AST broth tubes. The workflow next includes performing automated nephelometry to adjust the ID tube to a 0.5 or 0.25 McFarland ("McF"), adding AST indicator to the AST broth, transferring part of the sample to the AST broth, and mixing both tubes. The workflow next includes having the healthcare worker remove the processed ID and AST tubes and place them on an inoculation station having ID/AST Panels, such as Phoenix Panels, and inoculating the specimens in the Panels. See also U.S. Patent Application Publication No. 2008/0072664A1, the content of which is hereby incorporated in its entirety.

The Panels are then maintained within an ID/AST system (e.g., a Phoenix instrument) having a controlled environment (e.g., controlled temperature, humidity, light exposure, etc.) for a predetermined amount of time in order to promote microbial growth in the presence of the antimicrobial agent. The system typically includes an analysis capability in order to measure microbial growth in one or more microwells without disrupting the maintenance of a controlled environment. The system may also include a capability to report the analysis results to additional devices for further processing. Such system may include both ID and AST capability, or only ID or only AST capability. Moreover, even an ID/AST system can be run for only ID or only AST results. Panels See, e.g., U.S. Pat. Nos. 5,922,593, 6,096,272, 6,372,485, 7,115,384, and 6,849,422, the contents of which are hereby incorporated by reference in their entirety.

The various laboratory apparatus may be in communication with a data management system, such as the BD EpiCenter™, in order to provide a single location for a laboratory worker to monitor status and results from the various laboratory apparatus. Monitoring, analyzing and communicating microbiology data in a timely manner can directly impact patient care. However, obtaining, organizing and communicating information from the various laboratory apparatus is labor intensive. Current information systems can make even routine identification and AST testing difficult. Microbiologists, infection control officers, physicians and pharmacists need immediate access to patient focused information to rapidly identify and react to emerging resistance or HAI events. An improved method of collecting and analyzing data from the various instruments is needed.

BRIEF SUMMARY OF THE INVENTION

In one embodiment, the invention described herein is an automated system that both identifies microorganisms determined to be present in the sample and their antimicrobial resistance/susceptibility. The system has a first station that prepares a sample for both a mass spec (e.g., Maldi) process for microorganism identification and for antimicrobial susceptibility testing (AST). The mass spec process occurs at a second station and the AST occurs at a third station. The system has a user interface where samples are tracked so that the test results from the second and third stations are linked to the sample and the patient from whom the sample was obtained. The system also includes a station for determining if microorganisms are present in the sample and only those samples in which microorganisms are determined to be present are subjected to further processing and testing.

BRIEF DESCRIPTION OF THE DRAWINGS

FIG. 4 illustrates a concentrating pipette tip for use in the system of the present invention; and FIGS. 4A-D illustrate details of the concentrating pipette tip of FIG. 4.

DETAILED DESCRIPTION

The disclosure herein may refer to a Sample preparation apparatus (Sample prep or prep station hereinafter) as a "Phoenix AP", or an AST system as a BD Phoenix™ or refer to data management system with user interface as a "BD EpiCenter" system, or refer to a blood culture analysis apparatus as a "BD BACTEC™," or refer to a mass spectrometry system as Maldi, but it should be understood that the meaning of these terms is not limited to the apparatus having these trademarked names, but may include apparatus having a substantially similar functionality. Apparatus having substantially similar functionality may include the BacT/Alert (bioMerieux) and VersaTREK (Trek) blood culture systems, and the Vitek (bioMerieux) and MicroScan (Siemens Healthcare) ID/AST systems.

In one embodiment, the system described herein integrates the microbial identification capabilities of a Maldi instrument with the AST and data processing capabilities of a laboratory analysis or processing system such as the Phoenix, Phoenix AP, BACTEC, or EpiCenter systems.

In another embodiment, the Phoenix AP is modified to prepare not only the AST inoculum for the Phoenix Panels, but also prepare the same sample for the Maldi plate. This feature provides an automation benefit of positive identification for the sample prepared on the Maldi plate, by ensuring that the isolate applied to the Maldi plate is from the exact same sample used for antimicrobial susceptibility testing.

The Maldi, Sample prep, AST system, and/or blood culture instruments are in communication with a data management system such as the EpiCenter system. EpiCenter provides the real-time data access and analysis tools to improve patient care. EpiCenter is able to monitor, analyze and communicate microbiology data in a timely manner, thereby directly controlling, monitoring, and improving patient care. Phoenix produces the AST result, and the Maldi instrument produces the identification result. EpiCenter combines the results, and applies expert rules to produce the final ID/AST results for the sample. An example of such a system that applies expert rules is BDXpert™.

Figure 1:
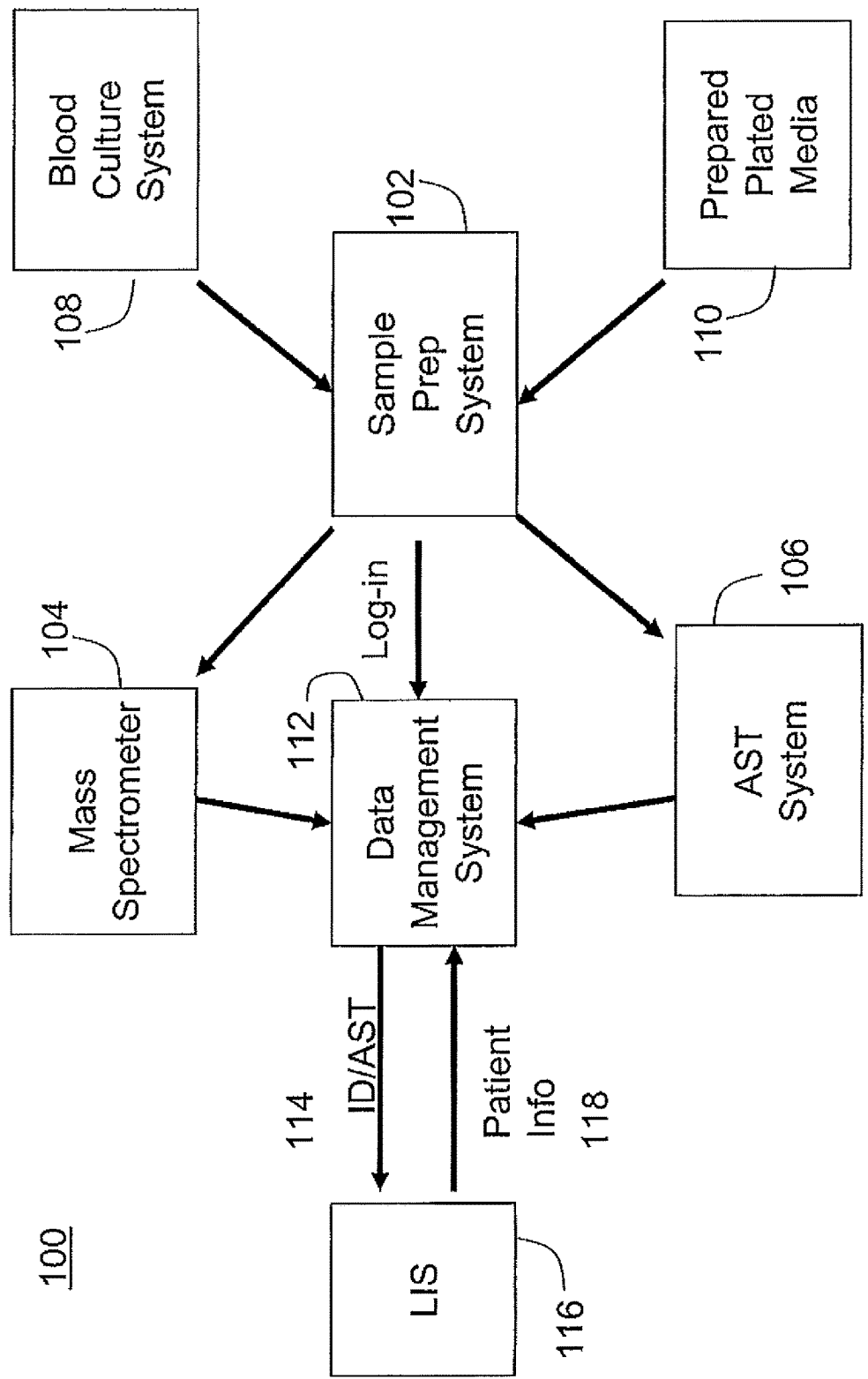
FIG. 1 shows a block diagram of a system to detect and analyze microbial samples, in accordance with one embodiment of the invention.

FIG. 1 shows a block diagram of a system 100 that detects and analyzes microbial samples, in accordance with an embodiment of the invention. The various components of system 100 include a Sample prep station 102 (such as a Phoenix AP), a mass spec instrument 104 (such as a MALDI-TOF), an AST system 106 (such as a Phoenix), a blood culture system 108 (such as a BACTEC instrument), prepared plated media 110 (e.g., manually prepared or prepared by a system such as the Innova), a data management system 112 (such as EpiCenter), and a Laboratory Information System 116 ("LIS") that receives data from the data management system 112 via ID/AST link 114, and which provides patient information to the data management system 112 via PT Info link 118.

In the system 100, the sample prep system is provided with bacteria, e.g., picked from a prepared plate or taken from a blood culture vial. In one embodiment in which a Phoenix AP is used, tubes are over inoculated with the bacterial sample. The tubes are advantageously used as the source for both ID and AST. This ensures that not only the same patient sample, but also the same isolate, is subject to the ID and AST testing.

The workflow connection between various components of system 100 is illustrated in FIG. 1. In general, the Sample prep station 102 prepares the sample, for both ID and AST, while the AST system 106 produces the AST result and the mass spec instrument 104 produces the ID result. Data management system 112 stores the ID result and AST result, optionally applying expert rules to produce the final combined ID/AST results for the sample, and also interacts with the LIS system.

Figure 2:
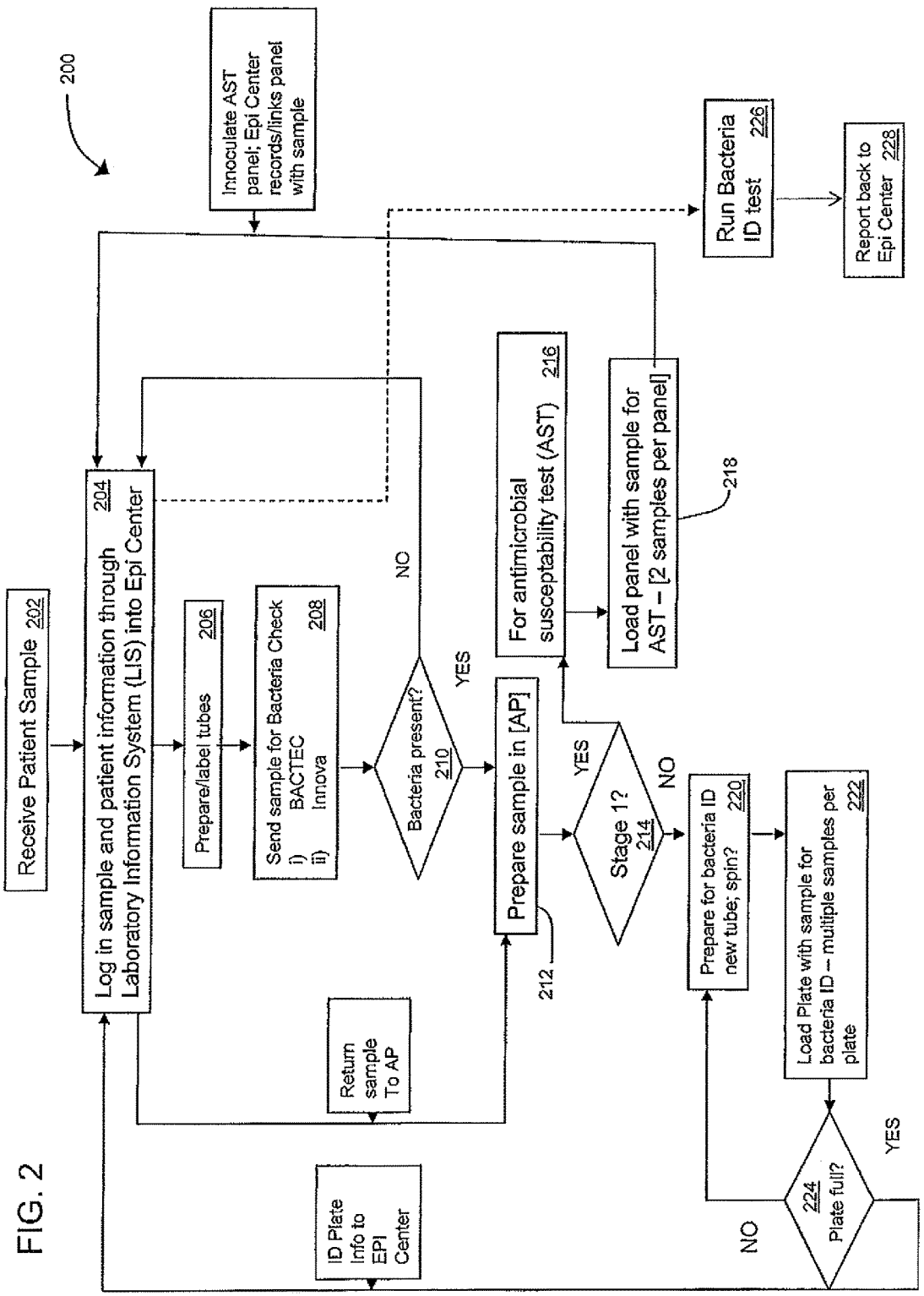
FIG. 2 shows a method of detecting and analyzing microbial samples, in accordance with one embodiment of the invention.

FIG. 2 illustrates a flow chart for the workflow process 200 of a first embodiment, and is described with reference to the exemplary system components illustrated in FIG. 1. Process 200 begins with receiving a patient sample at step 202. At step 204, a user enters sample and patient information through the LIS 116 into EpiCenter 112. Blood culture vials and/or prepared plates are prepared for testing at step 206, and then in step 208 these are sent to the BACTEC 108 for blood testing, and/or for automated (e.g., Innova 110) or manual lab for plate preparation. If no bacteria are detected in step 208, then that outcome is reported into the data management system, and no further processing occurs for those samples.

However, if bacteria are detected in step 208, then step 210 directs the sample to step 212 for preparation of a test tube sample in the Sample prep station 102. The sample prep station 102 then accesses information about the sample in step 214 to determine if the samples are at Stage 1. If the samples are stage 1 samples, the sample, referencing step 216, is prepared/sent for AST testing, and from there to step 218 for loading the AST panel with samples. For AST testing the sample is diluted in a first tube and a quantity of that sample is then transferred to a second inoculated tube for testing. The workflow proceeds back to step 204 to log sample and inoculated panels and start antimicrobial susceptibility analysis of these samples. When samples are returned from being logged, they are then evaluated to determine the stage of their analysis at the sample prep station 102.

If at step 214 it is determined that the samples are not at Stage 1, then the workflow passes to step 220 for preparing the samples for identification (i.e. Maldi). Step 220 may include a new test tube and an optional step of spinning the test tube (e.g., via use of a conical sample tube throughout the sample prep process) to concentrate the sample for Maldi testing. A concentrating pipette tube might also be used to concentrate the sample for Maldi. Control then passes to step 220, in which the test tube sample is loaded onto a Maldi plate and populated with additional samples until the plate is full. If the plate is full, as determined in step 224, the workflow proceeds back to step 204 where the samples are logged in and then proceed from there to the Bacteria ID test 226. The results of the Bacteria ID are reported back to the data management system (e.g., EpiCenter) in step 228.

In another aspect of the workflow illustrated in FIG. 2, after step 204, control may pass directly to step 212 in order to skip further bacteria testing at step 208 and go directly to preparing the sample at step 212 for AST testing.

Illustratively, the workflow to use system 100 begins with the receipt of an order, the order being either received by LIS 116 or entered directly into the data management system 112 for an ID test on the Maldi instrument 104 and an AST test using the AST system 106. Accession barcode labels may be printed out at the data management system 112 and applied to tubes loaded onto a test tube rack used by the Sample prep station 102.

Samples, once received, are evaluated for the presence of bacteria. In one embodiment the presence of bacteria in the sample is determined by the blood culture instrument that detects the presence of $CO_2$ as is known in the art. If the blood culture samples test positive for microorganisms, then the samples are identified for down stream processing—ID and AST. The Maldi and AST tests are run from the same sample.

In one example of AST sample preparation, the user over-inoculates one or more tubes with sample, e.g., a pellet from blood culture, or an isolate from a prepared plate (the isolate from the plate could be a subculture from a positive blood culture), and then places the tube on the Sample prep station 102. The Sample prep station 102 processes the tube, e.g., diluting the sample by adjusting to 4.5 ml 0.5 McF for a Phoenix AST test, and transfers aliquots (e.g. 25 1) to the AST tube. The Sample prep station 102 then records, into the RFID tag associated with the AST tube rack, the completion of stage 1.

The user then takes the rack to the data management system 112 and then inoculates an AST panel. The data management system 112 records the accession isolate information into the RFID tag on the rack. The user then puts the AST Panel into the AST system 106 for processing.

The user then puts the rack back onto the Sample prep station 102. The Sample prep station 102 will detect from the RFID tag that stage 1 is complete for that test tube rack. The user then optionally takes the rack to a spin-down station (not shown in FIG. 1), and manually spins down the sample in order to get the concentrated bacteria on the bottom of the tube for ID testing. Optionally, the sample tube into which the isolate or blood culture pellet is placed has a tapered shape that promotes concentration during the spin-down procedure. The tapered shape may be a cone shape. The user then pulls the concentrated bacteria out of the tube and inoculates a plate, which may be mounted on the deck of the Sample prep station 102. The Sample prep station 102 also adds a small amount of emulsion on top of the sample once the sample is in position on the Sample prep station 102, such emulsion known in the Maldi art. A concentrating pipette tube can also be used to populate the Maldi plate.

The Sample prep station 102 continues to do its stage 1 or stage 2 processing, depending on the information provided by the barcode or RFID of the rack located on the Sample prep station 102. The Sample prep station 102 continues to populate the Maldi plate until all sample positions on the plate are filled with sample.

Once all of the sample positions on the plate have been filled, the Sample prep station 102 records the entire Maldi plate configuration, including accession and isolate information that is useful for documenting the chain of custody, onto the RFID tag for the test tube rack that filled the Maldi plate.

The user then is prompted by the Sample prep station 102 to remove the plate and test tube rack. The test tube rack goes to the data management system 112, at which the RFID tag is read to receive the entire plate information, including the accession and isolate information.

The data management system 112 then transmits the plate configuration data to the Maldi instrument 104 for setup. When setup is ready, the user performs the ID testing on the Maldi instrument 104. When the test is complete, the Maldi instrument 104 electronically transmits plate results to the data management system 112. The plate results may include only positional results, and do not need to include the accession data.

The data management system 112 then associates plate data to the specimen and isolate data already recorded in the data management system 112 during an earlier step.

The ID results are then available for review and release at the data management system 112. The ID results can also be automatically reported via LIS 116 or by email depending on the configuration of the data management system 112.

An empiric advisor function, within data management system 112, may generate preliminary results of a focused antibiogram to guide empiric therapy choice prior to the availability of results from AST system 106. The preliminary results provided to LIS 116, or can be sent to an external monitoring system via email.

The AST system 106 then completes the AST results. The AST results and the ID results may be linked by an expert system within the data management system (e.g., EpiCenter) to provide the complete ID/AST test results. The AST results can be available for review and/or release at the data management system 112, or automatically reported via LIS 116, or reported by email to an external system, depending on the configuration of the data management system 112.

A second embodiment of a workflow to use system 100, and modifications to the components of system 100 that support the second embodiment of the workflow, are now described. Note that the second and subsequent embodiments may use the general workflow of FIG. 2, but without the stage 1 and stage 2 steps shown therein.

In this embodiment, as with previous embodiments, the workflow begins with the receipt of an order. The order is either received by LIS 116 or entered directly into the data management system 112 for an ID test on the Maldi instrument 104 and an AST test using the Sample prep station 102 and the AST system 106. Accession barcode labels may be printed out at the data management system 112 and applied to tubes loaded onto a test tube rack used by the Sample prep station 102.

The system loads an empty Maldi plate onto the test tube rack used by the Sample prep station 102. A user over-inoculates the sample tube in the rack, and places the rack into the Sample prep station 102. The Sample prep station 102 adjusts the tube concentration to whatever is required for the AST system 106, e.g., a 4.5 ml 0.5 McF. An aliquot is then transferred to the AST tube. The RFID tag on the test tube rack is updated with the adjustment result.

The Sample prep station 102 then uses a concentrating pipette tip to concentrate and dispense each sample from the sample tube to the Maldi plate for a predetermined number of times. The position of each isolate on the Maldi plate may correspond to the isolate position in the rack. The concentrating pipette tip is described in further detail below.

The Sample prep station 102 then adds a small amount of emulsion on top of each sample on the Maldi plate, and the rack RFID tag is updated with a flag indicating a Maldi plate was inoculated. A user then takes the rack to the data management system 112 and inoculates an AST panel from the AST tube.

The user scans rack positions of the data management system 112, the tube barcodes, and the panel barcodes for all rack positions, so the data management system 112 can associate accessions with panels. The user then scans the barcode on the Maldi plate so the data management system 112 can associate Maldi plate ID and position with each isolate. The user then puts the Panel into the AST system 106 for processing. The Maldi plate is removed from the test tube rack and is placed in the Maldi instrument 104 for processing.

After processing, the Maldi instrument 104 electronically transmits plate results (i.e., plate ID and positional results, without accession data) electronically to the data management system 112. The data management system 112 associates plate data to specimen and/or isolate data which is already recorded in the data management system 112. The ID results are then made available for review/release at the data management system 112, or auto reported via LIS 116 or email depending on the configuration of the data management system 112.

An empiric advisor function within the data management system 112 may generate preliminary results of a focused antibiogram to guide empiric therapy choice prior to AST results. Results may be provided to LIS 116 or provided by email to external systems.

When the AST system 106 completes the AST results, the ID from the Maldi instrument 104 is linked to make complete ID/AST results by using data management system 112 with expert system rules as described above.

When the AST analyzer 102 results are available, the results are provided for review and/or release at the data management system 112, or auto reported via LIS 116 or email depending on the configuration of the data management system 112.

A third embodiment of a workflow for system 100, and modifications to the components of system 100 in order to support this workflow, is now described.

In this aspect of the invention, the rack in the Sample prep station 102 holds a Maldi plate. The user places a high concentration, low volume tube in the rack. The Sample prep station 102 may also have the ability to accurately dispense concentrated samples onto a Maldi plate. The Sample prep station 102 may also have the ability to dispense a small amount of emulsion on top of each Maldi plate sample.

In this aspect of the invention, as with an earlier aspect of the invention, a workflow to use system 100 begins with the receipt of an order, the order being either received by LIS 116 or entered directly into the data management system 112 for an ID test on the Maldi instrument 104 and an AST test using the Sample prep station 102 and the AST system 106. Accession barcode labels may be printed out at the data management system 112 and applied to tube loaded onto a test Tube rack used by the Sample prep station 102.

The user then obtains an isolate from a culture plate prepared from the sample, or a pellet from a blood culture sample, and over-inoculates low volume tube in a rack. The low volume ensures a higher concentration of bacteria in any aliquot removed from the Tube. The user places the rack on the Sample prep station 102.

The Sample prep station 102 inoculates three spots on the Maldi plate from each tube in the test tube rack and writes the locations to the RFID tag of the test tube rack for each isolate. The Sample prep station 102 also scans the barcode on the Maldi plate and writes the plate ID to the RFID tag on the test tube rack. The Sample prep station 102 then adds a small amount of emulsion on top of each sample on the Maldi plate.

The Sample prep station 102 fills the tube to the minimum level needed for a nephelometer reading to ensure a proper concentration of bacterial colony forming units in the sample prior to AST testing.

The Sample prep station 102 then adjusts the concentration of the remaining sample to 0.5 McF, and transfers an aliquot to the AST tube. The RFID tag on the test tube rack is updated with adjustment result.

The user then takes the test tube rack to the data management system 112 and inoculates an AST panel. The user scans rack positions at the Sample prep station 102, tube barcode and panel barcode, for all rack positions, so the data management system 112 can associate accessions with panels. The data management system 112 then reads the Maldi plate ID and plate positions for each isolate from the rack RFID tag and makes appropriate associations with accessions. The user then puts the Panel into the AST system 106 for processing.

When the Maldi plate is full, or on some time schedule, the user removes the Maldi plate from the deck of the Sample prep station 102 and places it in the Maldi instrument 104 for processing, and adds a new Maldi plate to the deck of the Sample prep station 102. The new plate can be scanned by the Sample prep station 102 for its ID, or the user can log the plate in at the user interface of the Sample prep station 102.

The Maldi instrument 104 electronically transmits plate results (no accession data, just plate ID and positional results) electronically to the data management system 112.

The data management system 112 can then associate plate data to the specimen and/or isolate data already recorded in the data management system 112.

When ID results are available, the results can be reviewed and/or released at the data management system 112, or auto reported via LIS 116 or emailed to an external system depending on the configuration of the data management system 112.

An empiric advisor function in the data management system 112 generates preliminary results of a focused antibiogram to guide empiric therapy choice prior to results from the Sample prep station 102. Results are made available to LIS 116 or sent by email to an external system.

When the AST system 106 completes the AST results, the ID from the Maldi instrument 104 is linked to the AST results to provide complete ID/AST results by using data management system 112 with expert system rules.

When the AST analyzer 102 results are available, the results are provided for review and/or release at the data management system 112, or auto reported via LIS 116 or email depending on the configuration of the data management system 112.

In one embodiment of the invention, sample preparation on Sample prep station 212 is configured as a Single Pick system in which both bacterial identification and AST testing can be performed from a single bacterial isolate. This feature provides a more efficient system by eliminating the need for duplicate sample preparations for both AST testing and microorganism identification. In addition, this feature ensures data integrity by eliminating the possibility of identifying one bacterial strain and using a different strain for AST testing. In one example of this Single Pick system, once it has been determined that a microorganism is present in a sample (208 and 210), the sample is transferred to Sample prep station 212 in which the sample which tested positive for a microorganism is plated on a prepared media plate in order to grow single colonies of the microorganism. Within Sample prep station 212 a single isolate is picked from the media plate and an inoculum, or sub-culture, is prepared. In one embodiment of this example, a portion of this inoculum from a single colony pick is used for AST testing 216 while the remaining sample is used for identifying the microorganism 220 and 222. In a preferred embodiment, the AST testing is performed using the BD Phoenix and is carried out by any one of the methods described above. In another preferred embodiment the identification is done using Maldi analysis.

In yet another embodiment of the Single Pick system, a portion of the inoculum is concentrated in Sample prep station 212 prior to identification. This can be accomplished by using any method known in the art to concentrate bacterial culture samples. In one example, concentration is achieved by spinning the inoculum and re-suspending the microbial pellet into a smaller liquid volume.

Figure 3:
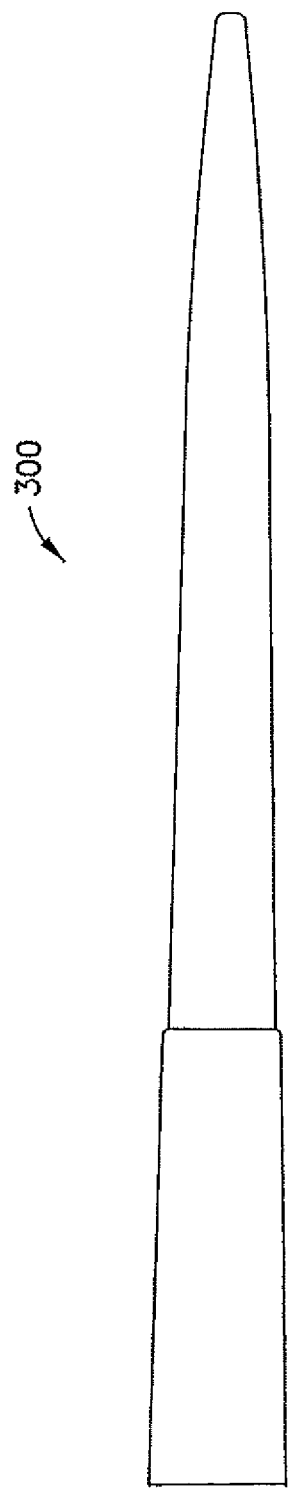
FIG. 3 shows a conventional pipette tip, as known in the art.

A feature that supports and facilitates the Single Pick system described herein for Sample prep station 212 is a pipette apparatus that can be used to further concentrate the sample for Maldi testing. A conventional pipette tip 300 is illustrated in FIG. 3, which is designed to prevent aerosols from being produced during the use of the pipette. As illustrated in FIG. 4, Sample prep station 212 may contain a pipette 400 that has a concentrating pipette tip 410 that contains a filter 420 and draws a portion of the inoculum 430 to be used for identification. The concentrating pipette tip can hold a fixed volume of sample below the filter 420 as shown in FIG. 4A. The inoculum 430 is concentrated by drawing up a volume greater than the fixed volume below the filter 420 so that the inoculum 430 and microorganism 440 are drawn through the filter 420 as shown in FIG. 4B and FIG. 4C. While drawing inoculum up into the pipette 400 above the filter 420, the microorganism 440 is trapped in the filter and below while the liquid inoculum 430 passes through the filter 420. The inoculum 430 is drawn up until the desired volume of liquid inoculum to be concentrated is above the filter. For example, if microorganism from 3 ml of sample is desired, 3 ml of inoculum would be drawn through the filter 420. In one embodiment, to concentrate the inoculum, a small amount of the liquid that is drawn above the filter is expelled in order to deposit microorganism from the filter 420 trapped below the filter 420 in a smaller volume of liquid than was drawn above the filter as shown in FIG. 4D. In one embodiment, the rack 450 in Sample prep station 212 holds a Maldi plate 460 and the concentrated microorganism 440 from the inoculum 430 is expelled onto the Maldi plate 460 for identification. In another embodiment, the concentrated microbial sample 440 is expelled from the concentrating pipette tip 410 by allowing the pipette tip 410 to come in direct contact with the Maldi plate 460. Direct contact allows the a small amount of liquid 430 to be wicked out of the pipette, carrying the concentrated microbial cells 440, and can be done without the need for expelling a volume of liquid from above the filter.

This improved pipette 440 is useful for improved concentration of a sample. For example, an inoculum concentration useful for the Phoenix panel is 0.5 McF or $1.5 \times 10^8$ cells per ml. The sample size for a typical Maldi instrument, however, may be 1 µl. A 1 µl aliquot from a 0.5 McFarland solution only yields $1.5 \times 10^5$ cells, which is near the low limit for detection ($1.0 \times 10^5$ cells) of typical Maldi instruments. Concentration of the inoculum for the Maldi plate is therefore desirable to obtain a reliable ID, but the level of concentration is not critical as long as it is well above the lower limit of detection.

Microfluidic devices routinely concentrate samples by flow of a low concentration sample through a filter to collect the material of interest on the filter, then reversing the flow through the filter forcing the material of interest off the filter to produce a high concentration sample. The modified pipette tip may include a filter material inside and very close to the tip. The filter is located close to the tip of the pipette in order to increase the amount of fluid within the pipette which passed through the filter, and decrease the amount of clued in the pipette which did not pass through the filter. The filter material is selected to strain cells from the fluid but does not retain the cells when the fluid flow is reversed to dispense the concentrated sample.

In one example of the Single Pick embodiment of the invention, a low concentration inoculum is drawn into the pipette tip through the filter material. Exemplary volume that is drawn into the pipette tip is 50 µl, the volume having a cell concentration of $1.5 \times 10^8$ cells per ml. Microorganisms (e.g. bacteria) in the sample collect on the filter material as the sample is drawn into the pipette tip. The flow is then reversed and a small fraction of the fluid that is drawn past the filter in the pipette tip is expelled taking the bacteria from the surface of the filter material and dispensing a high concentration sample from the pipette tip. With this modified tip a 1 µl sample containing roughly $7.5 \times 10^6$ cells (this translates to a concentration of $7.5 \times 10^9$ cells/ml) may be dispensed onto a Maldi plate.

A single filtering pipette tip could be used repeatedly for the same isolate to dispense as many Maldi plate spots as were required. The pipette tip is disposable, as it cannot be used for different isolates, due to cross contamination concerns.

In another embodiment that supports the system and workflows described herein, an improved rack for one embodiment of the AST processing station described herein (i.e. the Phoenix AP) that accommodates a Maldi sample plate may be provided to support the test method described herein.

The sample plate for a Maldi instrument normally contains 96 to 384 sample spots. The Phoenix AP instrument processes 4 isolates at a time. Clearly, the Phoenix AP instrument does not produce enough samples to fill a standard Maldi plate, even though the normal workflow for a Maldi instrument is to provide the Maldi instrument with multiple samples (normally 3) of the same isolate.

The rack used in the AST processing station, when used in a lab that has a Maldi instrument, can be modified to hold a small Maldi plate. The center isolate location of the AP rack can be replaced with a holder for the Maldi plate. The rack is modified to allow easy mounting and removal of the plate by the user, but must locate the plate accurately so the Phoenix AP instrument can dispense samples on the plate's spots.

Each plate used in the system bears a barcode with a unique plate ID so results from the Maldi instrument can be associated with results generated from the AP instrument.

An improved method for pipette tip positioning accuracy that supports the workflow and system described herein is also contemplated.

Using a pipette tip to dispense an isolate onto a Maldi plate involves a high level of positional accuracy for the pipette tip because of the small size of the spots on the Maldi plate. While the robot can position the pipette tip holder with a high degree of accuracy, the position of the working end of the pipette tip is not as accurate because of bends in the pipette tip.

To address the deficiencies in position accuracy caused by deformed pipette tips, two optical switches are added to the AP deck, one in a front-to-back orientation and the other in a left-to-right orientation. The robot can access a straight pipette-like position calibration tip that is the same length as the disposable pipette tips and fits the pipette tip holder like the disposable pipette tips. The position calibration tip has a high degree of positional accuracy relative to the pipette holder (i.e. the positional inaccuracies introduced by pipette tip deformity are avoided). The end of the position calibration tip is moved through the two optical switches and the position of the robot tip holder is recorded when each of the switches was triggered. This process accurately locates the optical switches on the AP deck relative to the pipette tip holder. That is the optical switches are aligned with the desired position of the pipette tip.

Each time a disposable pipette tip is picked up by the robot, the working end of the pipette tip is then passed through the two optical switches. The positional difference between the position for the calibration tip and the position for the disposable tip is measured and this defines an offset to be applied to all positions where the position of the disposable tip is to be determined.

An improved vision system for Maldi plate inoculation and barcode read that further supports the workflows and system described herein is also contemplated.

An alternative to the two optical switches described above is the use of a camera above the sample processing deck (e.g. the Phoenix AP described above). The camera captures images of the Maldi plate and the pipette tip and guides the tip to the spots on the plate. The camera also reads the barcode on the Maldi plate, and that information can be used to write the plate ID to the rack RFID tag.

As noted above, the components of the system described herein are adapted to use a sample processing station for preparing samples for both the Maldi and AST instruments (e.g. the BD Phoenix described above).

Running the Maldi instrument and the Phoenix instrument on the same sample requires the user to insure that the samples put into both instrument are from the same isolate. If two colonies are picked from a plate, one for Maldi testing and one for AST (e.g. Phoenix) testing, it is possible that the two colonies are not the same isolate. It is preferable for the Maldi and Phoenix samples to originate from the same colony. The embodiments described herein contemplate that the samples for Maldi and AST originate from the same tube prepared from the same colony or isolate.

The workflows and system described herein are further supported by using an improved, high concentration, low volume tube.

As noted above, the AST processing station (e.g. the AP instrument described above) processes the tube provided to achieve a 4.5 ml 0.5 McFarland suspension of the sample. This suspension is the starting point for inoculation of the AST tube and, optionally, the Maldi plate. When the AST instrument is only used for AST testing there is no need to achieve the 4.5 ml volume in the tube because the 4.5 ml volume is only needed for the inoculation of the ID portion of the Phoenix combination panel.

As noted above, the Sample prep station is adapted to provide a high concentration/low volume tube in which the organism colony is suspended that is suitable for both the AST and Maldi tests. This high concentration low volume tube would be used by the Sample prep station to directly inoculate the Maldi plate, assuming the concentration was high enough for the Maldi instrument. The volume of the tube contents would then be increased to the level that would allow a nephelometer reading of the suspension. The nephelometer reading would verify the concentration was appropriate for Maldi, and also begin the process of attaining the 0.5 McFarland concentration for the AST testing. The user would specify to the Sample prep station if the tube is needed for the inoculation of the ID side of an ID/AST combination panel. If no ID testing is to be performed on the AST instrument, the 4.5 ml ID inoculum volume is not required.

Furthermore, the 0.5 McFarland concentration for the AST sample is based on requirements of the ID side of the combination panel for the Phoenix instrument described above. In certain embodiments described herein, no ID is performed in the AST station. Therefore, the tube prepared in the Sample prep station could be left to contain a sample at higher concentration. To compensate for the higher inoculum concentration, a lower volume of sample is transferred from the tube to the AST tube. The transfer volume may be a function of measured inoculum density, such as an inverse proportion.

In further support of the workflows and systems described herein, an improved positive blood culture (PBR) process that provides sample directly to the sample prep station for both AST and Maldi tests is contemplated.

Specifically, the PBR processing involves spinning the blood culture bottle to concentrate the sample, washing the sample to eliminate the blood and media components, and spinning the sample again to produce a pellet of the organism. The pellet is similar to a colony on a plate that can be added to a tube to begin the process of preparing the sample in the Sample prep station for both Maldi test and AST.

The functions, apparatus, and system(s) described herein may be implemented by one or more processors that are programmed with software stored in a storage medium (not shown in the figures), the software being configured to perform a method in accord with an embodiment of the invention. The processor implementing various portions of the system may, for instance, be a single processor, or may be a part of the same processor (for example, one core in a multi core processor), or may be separate processors but in communication with each other, for instance by either a local electrical connection or by a networking connection that allows for a relatively longer remote connection. The processor is not limited and may also be implemented as an ASIC or other kind of processing device known in the art. The storage medium storing the software is not limited, and may include any physical and electronic medium used for electronic storage, such as a hard disk, ROM, EEPROM, RAM, flash memory, nonvolatile memory, or any substantially and functionally equivalent medium. The software storage may be co-located with the processor implementing an embodiment of the invention, or at least a portion of the software storage may be remotely located but accessible when needed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A system for testing a biological sample comprising:
a) a first module for detecting for presence of microorganisms in a sample, a second module comprising a mass spectrometer for detecting a type of bacteria in a sample and a third module comprising an antibiotic susceptibility testing instrument for determining an antibiotic susceptibility of the microorganism;
b) a data management module comprising a controller wherein the data management module receives data regarding the sample from the first, second and third modules and, in response to the received data controls preparing and handling of the sample in the system; and
c) an automated sample preparation module comprising:
i) a nephelometer adapted to receive a tube containing a suspension; and
ii) a pipette apparatus
wherein the automated sample preparation module is capable of preparing the biological sample for testing in the second module and the third module in response to a determination by the first module of the presence of microorganisms in the sample wherein the automated sample preparation module is adapted to communicate with the data management module and wherein the automated sample preparation module obtains a single isolated inoculum of the sample for testing in the second or third modules only if the sample meets a predetermined criteria indicating the presence of microorganisms in the sample in the first module and deposits the single isolated inoculum in the tube received by the automated sample preparation module to create a suspension in the tube, wherein a portion of the suspension in the tube is provided to both the second and third modules, wherein the nephelometer in the automated sample preparation module receives the tube carrying the suspension to determine a suspension concentration, wherein, when the nephelometer determines that the suspension is at the suspension concentration for AST testing the pipette apparatus of the automated sample preparation module dispenses a less concentrated sample from the tube containing the suspension made from the single isolated inoculum for testing in the third module and, the pipette apparatus dispenses a more concentrated sample from the tube containing the suspension onto a Maldi plate for testing in the second module, wherein, after the automated sample preparation module removes a portion of the suspension in the tube for used in the second module, the automated sample preparation module causes the pipette apparatus to dilute the concentration of the suspension in the tube for use in the third module to a predetermined concentration measured by the nephelometer.

2. The system of claim 1 wherein the sample automated preparation module is adapted to receive sample from a prepared plate or a culture vial.

3. The system of claim 1, wherein the predetermined concentration is 0.5 McFarland.

4. The system of claim 1 wherein the sample is received by the second module in more concentrated form after a portion of the suspension is received by the second module from the automated sample preparation module.

5. The system of claim 4 further comprising a concentrating pipette tip wherein the sample is concentrated with the concentrating pipette tip.

6. The system of claim 5 wherein the concentrating pipette tip has a proximate end with a tapered portion ending in an opening that defines a small volume, wherein a filter is disposed adjacent the tapered portion and a volume on a distal end of the filter that permits a volume of fluid to be drawn through the filter to concentrate those components of the fluid that are not drawn through the filter on the filter and in the tapered portion of the concentrating pipette tip.

* * * * *